(12) United States Patent
Keller et al.

(10) Patent No.: US 7,650,886 B1
(45) Date of Patent: Jan. 26, 2010

(54) ESOPHAGEAL AIRWAY MANAGEMENT DEVICE GUIDES

(76) Inventors: Christian Keller, Schneeburggosse 87, 6020 Innsbruck (AT); Joseph R. Brimacombe, Coral Towers The Espianade 255, 4870 Cairns (AU)

( * ) Notice: Subject to any disclaimer, the term of this patent is extended or adjusted under 35 U.S.C. 154(b) by 270 days.

(21) Appl. No.: 10/791,895

(22) Filed: Mar. 4, 2004

(51) Int. Cl.
A61M 16/00 (2006.01)
A61M 25/00 (2006.01)
A62B 9/06 (2006.01)

(52) U.S. Cl. ............................ 128/207.14; 128/207.15; 128/207.17; 604/523; 604/525; 604/530

(58) Field of Classification Search ............ 128/207.14, 128/207.15, 200.26, 200.25, 207.17; 604/523–525, 604/530, 536
See application file for complete search history.

(56) References Cited

U.S. PATENT DOCUMENTS

| | | | |
|---|---|---|---|
| 3,508,554 A * | 4/1970 | Sheridan | 604/523 |
| 4,231,365 A | 11/1980 | Scarberry | |
| 4,329,983 A | 5/1982 | Fletcher | |
| 4,632,112 A | 12/1986 | Matthews | |
| 4,688,568 A | 8/1987 | Frass et al. | |
| 4,793,327 A * | 12/1988 | Frankel | 600/194 |
| 4,825,858 A | 5/1989 | Frankel | |
| 5,171,232 A * | 12/1992 | Castillo et al. | 604/529 |
| 5,339,805 A | 8/1994 | Parker | |
| 5,499,625 A | 3/1996 | Frass et al. | |
| 5,546,936 A * | 8/1996 | Virag et al. | 128/207.14 |
| D398,989 S * | 9/1998 | Ashlin | D24/115 |
| 5,919,183 A * | 7/1999 | Field | 604/530 |
| 6,053,166 A * | 4/2000 | Gomez | 128/200.26 |
| 6,055,984 A * | 5/2000 | Brain | 128/207.14 |
| 6,164,277 A * | 12/2000 | Merideth | 128/207.14 |
| 6,439,232 B1 | 8/2002 | Brain | |
| 6,503,353 B1 * | 1/2003 | Peterson et al. | 156/86 |
| 6,568,388 B2 | 5/2003 | Christopher | |
| 6,637,435 B2 * | 10/2003 | Ciaglia et al. | 128/207.29 |
| 7,115,183 B2 * | 10/2006 | Larson et al. | 156/293 |
| 7,141,046 B2 * | 11/2006 | Perkins et al. | 604/514 |
| 2002/0195103 A1 | 12/2002 | O'Mara | |
| 2003/0062039 A1 | 4/2003 | Sniadach | |

OTHER PUBLICATIONS

George A. Arndt, Adam J. Cambray, Jon Tomasson, "Intubation Bougie Dissection of Tracheal Mucosa and Intratracheal Airway Obstruction".
2008 International Anesthesia Research Society, Anesthesia & Analgesia, vol. 107:603-604 (2 pp.) Aug. 2008.

* cited by examiner

Primary Examiner—Patricia Bianco
Assistant Examiner—Brandon Jackson
(74) Attorney, Agent, or Firm—Shlesinger, Arkwright & Garvey LLP

(57) ABSTRACT

And the esophageal airway management device guide insertable in a patient's trachea with minimum throat, esophageal or tracheal injury having a distal section softer than an intermediate section which also may have a proximal section softer than the intermediate section.

13 Claims, 3 Drawing Sheets

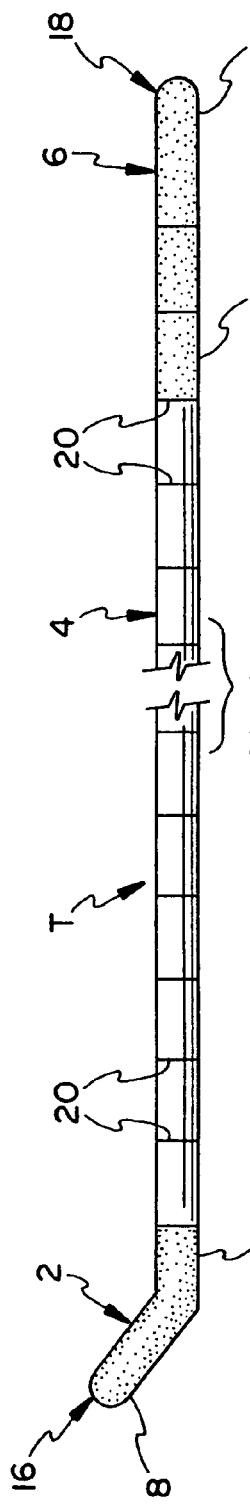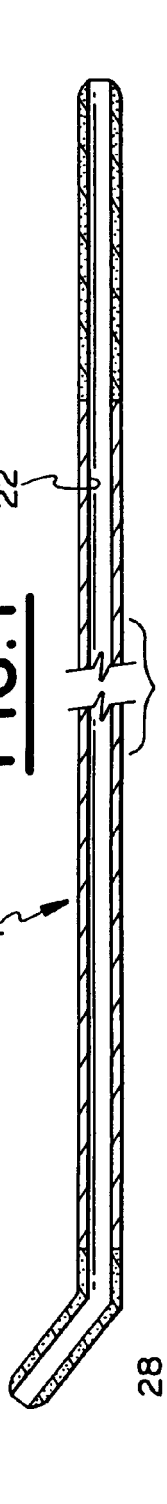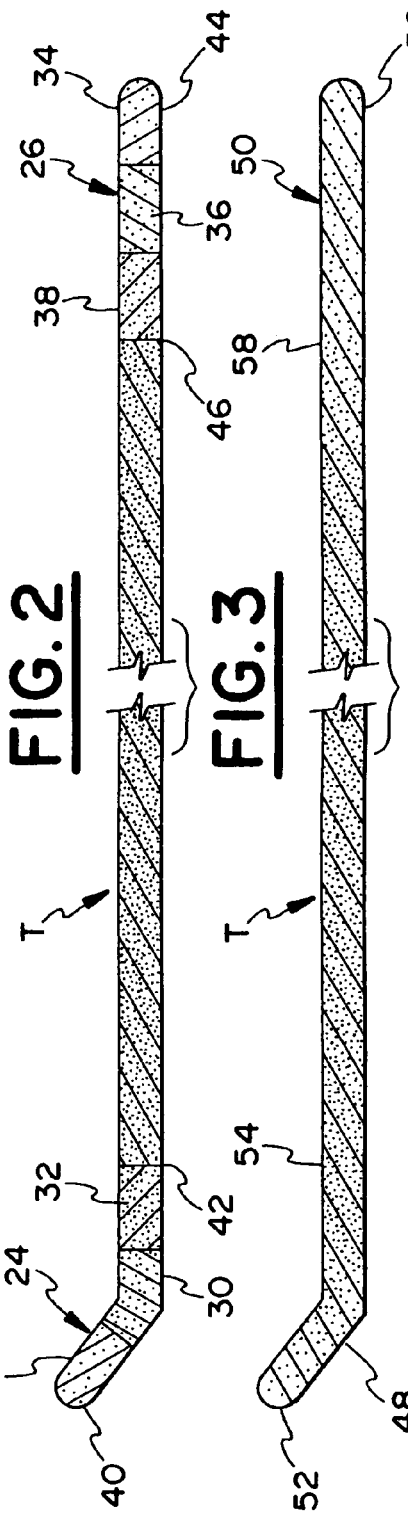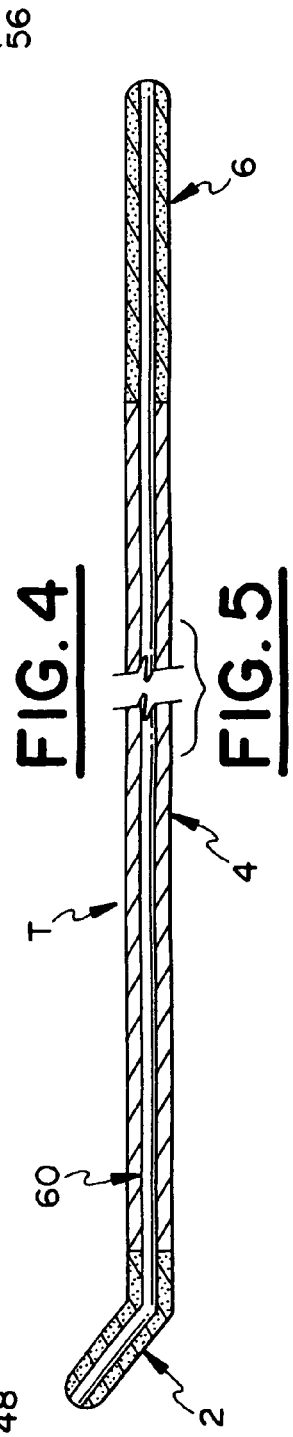

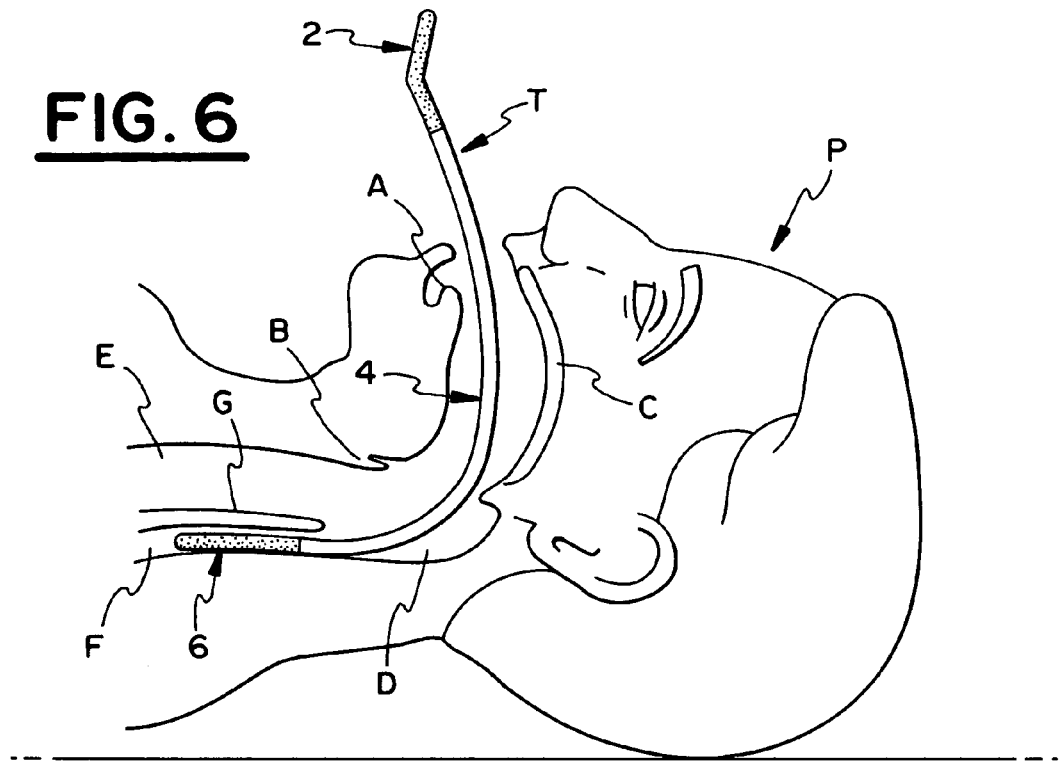
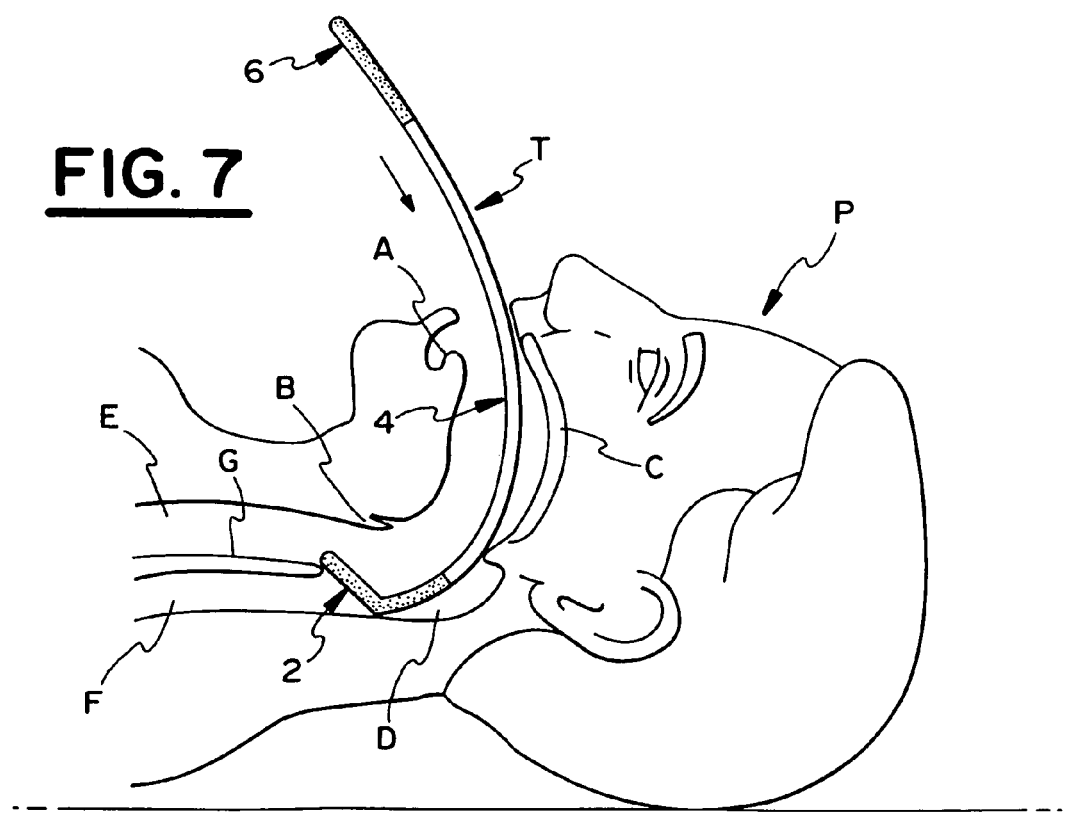

ESOPHAGEAL AIRWAY MANAGEMENT DEVICE GUIDES

FIELD OF THE INVENTION

This invention relates to esophageal airway management device guides which are insertable inside (subglottic) and outside (extraglottic) a patient's esophagus or trachea with minimum throat esophageal or tracheal injury.

BACKGROUND OF THE INVENTION

Esophageal airway guides used in the field of airway management in both humans and other mammals have been developed in the past twenty or more years for positioning extraglottic airway devices (EAD) as well as subglottic airway devices (SAD) which provide enough rigidity to guide the EAD or the SAD around the back of the mouth to help reduce the risk of tissue injury. In some instances such as in Scarberry U.S. Pat. No. 4,231,365; Parker U.S. Pat. No. 5,339,805 and Christopher U.S. Pat. No. 6,568,388, the guide has a generally preformed curvature which when positioned, assists in manipulating the airway management devices into position. Saladach U.S. publication 2003/0062039 of Apr. 3, 2003; Gomez U.S. Pat. No. 6,053,166; Frankel U.S. Pat. No. 5,793,327 and Fletcher U.S. Pat. No. 4,329,983 provide a mechanical mechanism for manipulating the end of the guide from outside of the patient in order to position the airway management devices. Flexible guide members have also been used such as in Matthews U.S. Pat. No. 4,632,112; Frankel U.S. Pat. No. 4,825,858 and Field U.S. Pat. No. 5,919,183. Although the above devices disclosed in the patents assist in positioning and/or reduction of injury, the medical profession states that substantial improvement over present devices in positioning as well as in reducing injury is required.

OBJECTS AND SUMMARY OF THE INVENTION

It is an object of this invention to provide an esophageal airway management device guide which is insertable inside (subglottic) and outside (extraglottic) a patient's trachea substantially reducing throat, esophageal or tracheal injury over the present existing art.

Another object of this invention is to provide an esophageal airway management device which has a dual function for an insertion into the trachea or into the esophagus merely by flipping the guide to present the other end thereof.

A further object of this invention is to provide an esophageal airway management device guide which can be readily manufactured with a minimum amount of cost from inexpensive readily available plastic materials.

Still a further object of this invention is to provide an esophageal airway management device guide which is readily removable after positioning of the airway management device.

Another object of this invention is to provide an esophageal airway management device guide which may be easily manipulated by the physician and which has application both to humans and animals including infants and adults.

Yet another object of this invention is to provide an esophageal airway management device guide which permits incorporation of an optical mechanism such as a fiber optic device.

Still another object of this invention is to provide an esophageal airway management device guide made from plastic which is opaque for purposes of radiological observation.

A further object of this invention is to provide an esophageal airway management device guide which may be tubular to permit venting or detection of gases and fluids.

Still a further object of this invention is to provide an esophageal airway management device guide which provides the physician with indicating means for clearly determining the exact position of the end of the guide in the patient's throat.

In summary, this invention provides an esophageal airway management device guide which minimizes injury as well as facilitating placement of the guide in the patient with accuracy as well as providing the physician with a single device which has a dual function in that it can be used for positioning either in the trachea or the esophagus.

These and other objects of this invention will be apparent from the following description and from the drawings which are as follows:

DETAILED DESCRIPTION OF THE DRAWINGS

FIG. 1 is a side elevational view of the insert of this invention broken away to show indeterminant length;

FIG. 2 is a cross sectional view of a modified form of this invention broken away to show indeterminant length;

FIG. 3 is a side elevational view of a modified version of this invention broken away to show indeterminant length;

FIG. 4 is a side elevational view of yet another modification of this invention broken away to show indeterminant length;

FIG. 5 is a cross sectional modification showing a fiber optic device mounted in the insert broken away to show indeterminant length;

FIG. 6 is a fragmentary schematic in which a portion is shown in cross section positioning the insert into the esophagus for subsequent positioning of the airway devices;

FIG. 7 is a fragmentary schematic in which a portion is shown in cross section just prior to positioning the insert into the trachea for subsequent positioning of the airway devices;

FIGS. 1 Through 5

Figure 8:
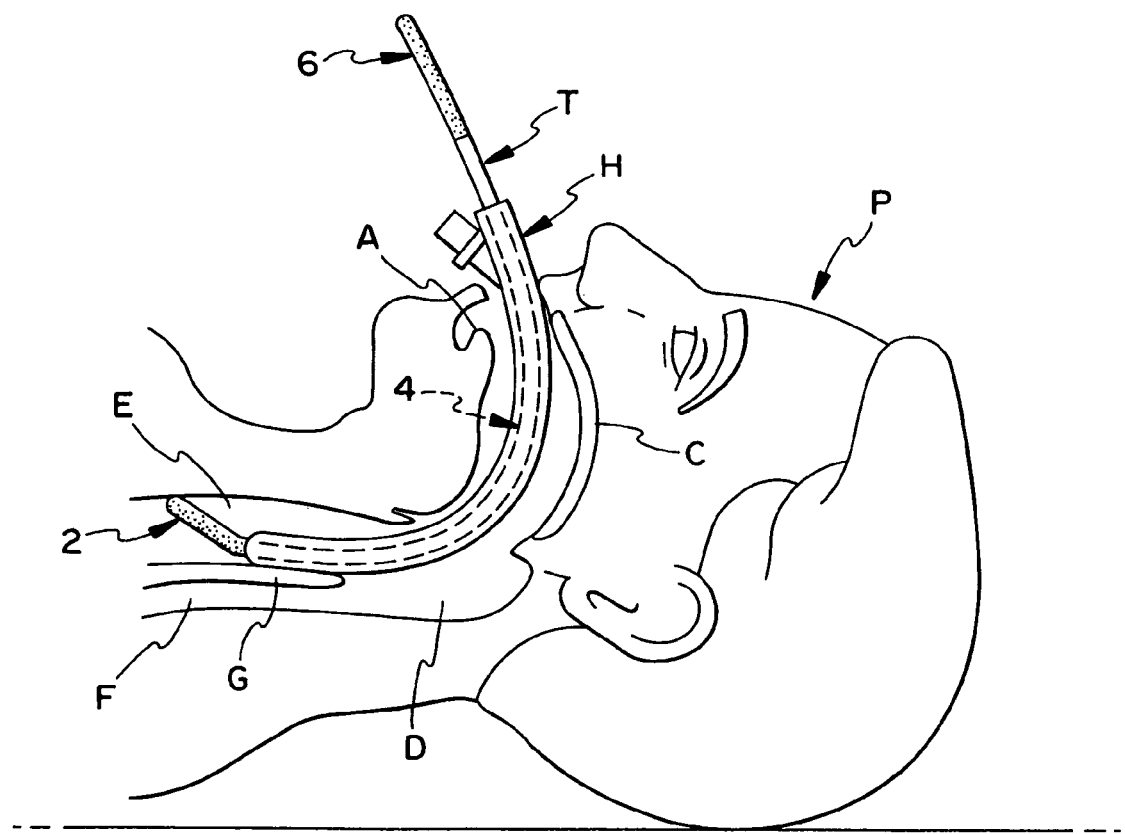
FIG. 8 is a schematic view showing an airway device mounted on the insert in the patient prior to withdrawal of the insert.

In FIG. 1, the insert or guide T has a proximal or first throat insertable end section 2, an intermediate section 4, and a distal or second throat insertable end section 6. The sections 2, 4, and 6 are integrally connected by fusion, gluing or other means such as extrusion, injection molding or casting. The angled proximal section 2 has a front portion 8 and a rear portion 10. The non-angled distal section 6 has a front portion 12 and a rear portion 14. The insert or guide T is of a plastic material including medical grade polyvinyl chloride (PVC), a medical grade silicone plastic, and a medical grade polyethylene though it may be of other plastic malleable and ductile materials. The intermediate section 4 is of a stiffer malleable and ductile material than the softer malleable and ductile material of the proximal and distal sections 2 and 6 and has a hardness between about 50 SHORE A to about 90 SHORE D. The proximal section 2 and the distal section 6 have a SHORE hardness approximately 20% to approximately 30% less than the selected hardness of the intermediate section 6. The proximal front portion 8 has an end tip 16 and the distal front portion has an end tip 18. End tip 16 and end tip 18 are each blunt, as shown in FIG. 1, and in each of the other FIGS. 2-8. The insert or guide T is provided with depth indicating means 20 which may be measuring indicia or color coding or other marking including indenting to permit the physician to determine the position of the end tip 16 of the proximal front portion or the end tip 18 of the distal front portion depending upon which is inserted into the patient.

The insert or guide T is slender and may be solid or tubular for the purpose of exhausting gases or fluids. The insert or guide T has an overall length of approximately 30 cm to about 90 cm with a diameter of from about 2 mm to about 5 mm depending on the patient's size. The patient may be an infant, child or an adult and size will be the determining factor as to the length of the insert or guide T.

In FIG. 2, the insert or guide T is shown in cross section tubular having a passageway 22 for transfer of fluids or gases. In FIGS. 1 through 5, the proximal section 2 is bent upwardly at an angle from about 25° to about 45° and preferably about 35° for insertion into the trachea. The proximal section front portion extends from about 0.5% to about 20% of the total length of the slender insert or guide T. The length of the soft distal section 6 extends from about 0.5% to about 50% of the total length of the slender insert or guide T.

In FIG. 1, the soft proximal and distal sections 2 and 6 are of a constant softness from the end tips 16 and 18 through the rear portions 10 and 14. In FIG. 3, the proximal and distal sections 24 and 26 show a series of steps 28, 30, 32, 34, 36, and 38. Each successive step from the front end tip 40 to the rear 42 of the proximal section 24 and from the distal section 26 from the front end tip 44 to the rear 46 is slightly harder than the previous step. The proximal sections 24 and 26 shown with three(3) steps may have two or more.

In FIG. 4, the insert or guide T has a proximal section 48 in which the hardness increases gradually from the tip 52 to the rear 54. The distal section 50 also has the hardness increasing from tip 56 to the rear 58.

In FIG. 5, the insert or guide T carries a fiber optic device 60 which may be embedded or otherwise carried by the insert or guide T.

As in FIG. 1, the intermediate sections of FIGS. 2-5 are of a stiff malleable and ductile material having a hardness between about 50 SHORE A and about 90 SHORE D with the proximal and the distal sections being softer malleable and ductile sections with a hardness approximately 20% to approximately 30% less than the selected hardness of the intermediate section.

FIGS. 6, 7, and 8

FIG. 6 shows a reclining person P. Outlined is the tongue A, the epiglottis B, the mouth C, the throat D, the trachea E, the esophagus F, and the corniculata and arytenoid cartilage G which separates the trachea E from the esophagus F. The insert or guide T is shown positioned in the esophagus F. The distal section 6 which is softer than the intermediate section 4 passes through the throat and into the esophagus with minimal injury to the tissue. The intermediate section 4 follows the distal section 6 without tissue injury. Once the insert or guide T is positioned, the esophageal airway management device is slid onto the insert or guide T and goes into position in the esophagus with minimal injury. Note the positioning of the esophageal airway management device H in FIG. 8. Various airway management devices such as shown in the aforementioned references may be used. FIG. 7 shows the insert or guide T about the positioned in the trachea. The angled proximal section 2 being soft, engages the cartilage G which guides the insert or guide T into the trachea with minimal tissue injury. Obviously the airway management device H is slipped down the insert or guide T into position in the same manner as generally illustrated in FIG. 8 with the insert or guide T in position in the trachea. Once the airway management device H is positioned, the insert or guide T is withdrawn therefrom.

It is to be noted that the accuracy of the positioning is improved over prior art devices because of the depth indicating means 20 on the insert guide T.

The guide T when used with the bent section e.g. 2 for insert into the trachea, is easily withdrawn from the airway management device H, since removal reshapes the bent section to a straight or curved section during withdrawal.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

What is claimed is:

1. An esophageal airway management device guide for positioning extraglottic (EAD) and subglottic (SAD) airway devices insertable in a patient's trachea or esophagus and configured for preventing throat, esophageal or tracheal injury comprising:

a) a slender dual function flippable insert having a length from about 30 cm to about 90 cm and a diameter from about 2 mm to about 5 mm depending on the patient's size;

b) said insert being an integrally connected slender dual function flippable insert having integrally connected first angled and second non-angled throat insertable end sections separated by an intermediate section;

c) said first and second throat insertable end sections each having front and rear portions;

d) said first insertable end section's front portion extending from about 0.5% to about 20% of the total length of said slender insert and said second insertable end sections' front portion extending from about 0.5% to about 50% of the total length of said slender insert;

e) said first insertable and second insertable end sections' front portion having an end tip;

f) each of said first insertable and second insertable end sections' end tip being a blunt end tip;

g) said first insertable and second insertable end sections comprising a soft, malleable and ductile material extending from said first insertable and second insertable end sections' front portion end tip through said first insertable and second insertable end sections' rear portion;

h) said intermediate section positionable in the patient's throat comprising a stiff, malleable and ductile material stiffer than said soft malleable and ductile first and second insertable end sections and having a selected hardness of between about 50 SHORE A to about 90 SHORE D;

i) said first and second insertable end sections having a SHORE hardness approximately 20% to approximately 30% less than said selected hardness of said intermediate section;

j) said first insertable end section insertable into a patient's trachea;

k) said second insertable end section insertable into a patient's esophagus; and l) said first insertable end section is bent at an angle of about 25° to about 45° with respect to said intermediate section.

2. An esophageal airway management device guide as in claim 1, and wherein:

a) said slender insert is a tube.

3. An esophageal airway management device guide as in claim 1, and wherein:

a) said slender insert is solid.

4. An esophageal airway management device guide as in claim 1, and wherein:
   a) said first and second insertable end distal sections' SHORE hardness is constant from said first and second insertable end sections' front portion end tip through said first and second insertable end sections' rear portion.

5. An esophageal airway management device guide as in claim 1, and wherein:
   a) said first and second insertable end sections' SHORE hardness increases continuously from said first and second insertable end sections' front portion end tip through said first proximal and second insertable end sections' rear portion.

6. An esophageal airway management device guide as in claim 1, and wherein:
   a) said first and second insertable end sections' SHORE hardness increases in a series of steps from said first and second insertable end sections' front portion end tip through said first and second insertable end sections' rear portion.

7. An esophageal airway management device guide as in claim 1, and wherein:
   a) said plastic is from the group consisting of a medical grade polyvinyl chloride (PVC), a medical grade silicone plastic, and a medical grade polyethylene.

8. An esophageal airway management device guide as in claim 1, and wherein:
   a) said slender insert includes insertion depth indicating means.

9. An esophageal airway management device guide as in claim 1, and wherein:
   a) said insertion depth indicating means includes measuring indicia.

10. An esophageal airway management device guide as in claim 8, and wherein:
    a) said insertion depth indicating means is color coding.

11. An esophageal airway management device guide as in claim 1, and wherein:
    a) said first insertable end section is bent at an angle of about from 25° to about 45° with respect to said intermediate section and upon withdrawal is reshaped.

12. An esophageal airway management device guide as in claim 1, and wherein:
    a) said first insertable end section is bent at an angle of about 35° with respect to said intermediate section.

13. An esophageal airway management device guide as in claim 11, and wherein:
    a) said bent first insertable end section conforms to said esophageal management device during insertion and withdrawal.

\* \* \* \* \*